United States Patent [19]

Ramey et al.

[11] 4,056,507
[45] Nov. 1, 1977

[54] HINDERED PIPERIDINE CARBOXYLIC ACIDS, METAL SALTS THEREOF AND STABILIZED COMPOSITIONS

[75] Inventors: Chester E. Ramey, Spring Valley; John J. Luzzi, Carmel, both of N.Y.

[73] Assignee: Ciba-Geigy Corporation, Ardsley, N.Y.

[21] Appl. No.: 633,201

[22] Filed: Nov. 19, 1975

Related U.S. Application Data

[62] Division of Ser. No. 429,232, Dec. 28, 1973, Pat. No. 3,920,661.

[51] Int. Cl.² ............... C08K 5/34; C08D 211/18; C07D 401/00
[52] U.S. Cl. ............... 260/45.8 N; 252/400 A; 252/400 R; 252/406; 260/45.75; 260/45.75 M; 260/45.75 N; 260/45.75 P; 260/45.75 Q; 260/45.75 R; 260/45.8 NT; 260/45.85 N; 260/270 C; 260/293.63; 260/293.66; 260/293.69; 260/293.86; 260/632.5
[58] Field of Search ............ 260/45.8 N, 293.63, 260/293.69, 293.66, 293.86, 270 C; 252/400 R, 400 A, 406

[56] References Cited

U.S. PATENT DOCUMENTS

| | | | |
|---|---|---|---|
| 3,120,540 | 2/1964 | Melzer | 260/293.63 |
| 3,640,928 | 2/1972 | Murayama | 260/18 N |
| 3,840,494 | 10/1974 | Murayama | 260/293.66 |

Primary Examiner—H.S. Cockeram
Attorney, Agent, or Firm—Nestor W. Shust

[57] ABSTRACT

Compounds having the formula

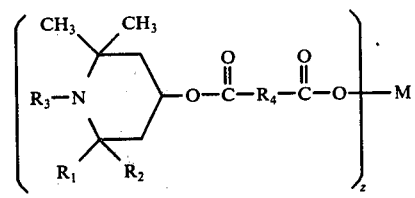

wherein
$R_1$ and $R_2$ are lower alkyl or cycloalkyl,
$R_3$ is hydrogen, alkyl, methoxyethyl, alkenyl, propargyl, benzyl or alkyl substituted benzyl,
$R_4$ is alkylene, alkyl-thio-alkyl or alkyl-oxo-alkyl,
M is hydrogen or a metal, and
z has a value of from 1 to 4, are good light stabilizers. The carboxylic acids are prepared, for example, from 2,2,6,6-tetramethyl-piperidin-4-ol and sebacic acid to give o-mono(2,2,6,6-tetramethyl-piperidin-4-ol)sebacate. The metal salts of the acids are readily prepared by reacting the acids or their salts with a reactive form of the metal or metal complex.

26 Claims, No Drawings

HINDERED PIPERIDINE CARBOXYLIC ACIDS, METAL SALTS THEREOF AND STABILIZED COMPOSITIONS

BACKGROUND OF THE INVENTION

This is a division of application Ser. No. 429,232 filed on Dec. 28, 1973, now U.S. Pat. No. 3,920,661.

This invention relates to the stabilization of organic material normally tending to deteriorate. In particular, the invention relates to the protection of synthetic polymers against the harmful degradative effects, such as discoloration and embrittlement caused by exposure to light, especially ultraviolet light.

It is known that actinic radiation, particularly in the near ultraviolet region, has a deleterious effect on both the appearance and properties of organic polymers. For example, normally colorless or light colored polyesters yellow on exposure to sunlight as do such cellulosics as cellulose acetate. Polystyrene discolors and cracks, with accompanying loss of its desirable physical properties when exposed to actinic light, while vinyl resins, such as polyvinyl chloride and polyvinyl acetate spot and degrade. The rate of air oxidation of polyolefins such as polyethylene and polypropylene is materially accelerated by ultraviolet light.

It has been proposed to stabilize polymeric materials against ultraviolet light deterioration by the use of various types of ultraviolet absorbers. Thus, U.S. Pat. No. 3,004,896 discloses for this purpose 2(2-hydroxyphenyl)benzotriazole derivatives, while U.S. Pat. No. 3,189,630 discloses certain metal salts of hydroxybenzoic acids which are useful as actinic stabilizers in synthetic polymers.

Additionally, in U.S. Pat. No. 3,120,540 there is discussed the reaction of substituted 4-piperidinol compounds with acid anhydrides having the formula

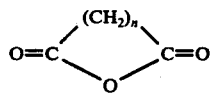

where $n$ is 1 to 4, to yield bis(polymethyl)-4-piperidinol alkanoates. In the example of this patent the probable formation of

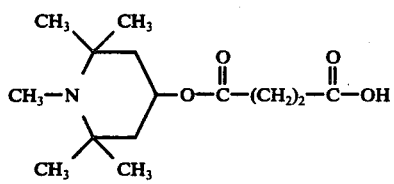

is mentioned as an intermediate in the synthesis of the bis(hydrogen sulfate)salt of bis(1,2,2,6,6-pentamethyl-4-piperidyl)succinate. The compounds of U.S. Pat. No. 3,120,540 are taught to possess significant pharmacological activity in lowering blood pressure. We have now found that certain acid half esters of hindered piperidines stabilize organic substrates against the degradative effect of ultraviolet light and that the degree of stabilization achieved is significantly greater in the case of higher acid half esters than in the case of the above-mentioned succinic acid half-ester. We have also found that certain hetero-atom containing piperidine half-esters and salts of piperidine half esters are useful as stabilizers of organic materials.

DETAILED DISCLOSURE

The present invention is accordingly directed to a new class of ultraviolet light stabilizers which consist of a compound of the formula

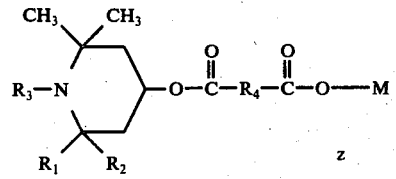

wherein
$R_1$ and $R_2$ independently of each other are straight- or branched-chain alkyl having from 1 to 6 carbon atoms, or together with the carbon to which they are bound form a cyclopentyl or cyclohexyl ring, which is unsubstituted or substituted with a methyl group, $R_3$ is hydrogen, alkyl having 1 to 12 carbon atoms, $\beta$-methoxyethyl, alkenyl having 3 to 4 carbon atoms, propargyl, benzyl or alkyl substituted benzyl, $R_4$ is straight or branched-chain alkylene having 5 to 8 carbon atoms, or the group

wherein Y is oxygen or sulfur and $m$ and $n$ independently of each other are an integer from 1 to 3, M is hydrogen or a metal selected from the group consisting of barium, nickel, manganese, calcium, zinc, iron, sodium, cobalt tin and dialkyl tin, and $z$ has a value of from 1 to 4, the value of $z$ being the same as the available valence of M.

Examples of $R_1$ and $R_2$ are methyl, ethyl, iso-propyl, n-butyl and n-hexyl. Preferably, $R_1$ and $R_2$ are each a methyl group. Representative of $R_1$ and $R_2$ as cycloalkyl groups are cyclohexyl, cyclopentyl, 2-methyl, 3-methyl and 4-methylcyclohexyl, and 2-methyl and 3-methylcyclopentyl. The preferred cycloalkyl groups are cyclohexyl and 2-methylcyclohexyl. Most preferably, $R_1$ and $R_2$ are each a methyl group.

Substituent $R_3$ can be hydrogen, alkyl having 1 to 12 carbon atoms, preferably alkyl having 1 to 4 carbon atoms, methyl being particularly preferred, $\beta$-methoxyethyl, alkenyl having 3 to 4 carbon atoms, preferably allyl, propargyl, benzyl or alkyl substituted benzyl. Hydrogen and methyl are particularly preferred.

Examples of $R_3$ are hydrogen, methyl, ethyl, n-propyl, isopropyl, n-butyl, isobutyl, n-hexyl, n-octyl, n-dodecyl, alkyl, $\alpha$-methallyl, propargyl, benzyl, $\alpha$-methylbenzyl, p-methylbenzyl and $\alpha$, p-dimethylbenzyl.

The preferred alkylene residue $R_4$ is straight-chain alkylene having 5 to 8 carbon atoms, or the group $(CH_2)_mY(CH_2)_n$ wherein Y is oxygen or sulfur and $m$ and $n$ independently of each other are 1 or 2.

Among the substituents represented by M, hydrogen, nickel and manganese are preferred. Particularly preferred are hydrogen and nickel.

This invention also relates to compositions of matter which are stabilized against ultraviolet light deterioration which comprises a synthetic organic polymer normally subject to ultraviolet deterioration containing from about 0.005% to 5% by weight of the polymer of the compounds of formula I and preferably from 0.01 to 2% by weight.

The compounds as represented by formula I, can be used in combination with other light stabilizers such as 2(2-hydroxyphenyl)benzotriazoles, 2-hydroxybenzophenones, nickel complexes and benzoates.

The compounds of this invention are stabilizers of organic material normally subject to thermal, oxidative or actinic light deterioration. Materials which are thus stabilized include synthetic organic polymeric substances including homopolymers, copolymers, and mixtures thereof, such as vinyl resins formed from the polymerization of vinyl halides or from the copolymerization of vinyl halides with unsaturated polymerizable compounds, e.g., vinyl esters, $\alpha,\beta$-unsaturated acids, $\alpha,\beta$-unsaturated esters, $\alpha,\beta$-unsaturated ketones, $\alpha,\beta$-unsaturated aldehydes and unsaturated hydrocarbons such as butadienes and styrene; poly-$\alpha$-olefins such as high and low density polyethylene, cross-linked polyethylene, polypropylene, poly(4-methylpentane-1 and the like, including copolymers of $\alpha$-olefins; such as ethylene-propylene copolymers, and the like; dienes such as polybutadiene, polyisoprene, and the like, including copolymers with other monomers; polyurethanes such as are prepared from polyols and organic polyisocyanates, and polyamides such as polyhexamethylene adipamide and polycaprolactam; polyesters such as polyethylene terephthalates; polycarbonates such as those prepared from bisphenol-A and phosgene; polyacetals such as polyethylene terephthalate polyacetal; polystyrene, polyethyleneoxide; polyacrylics such as polyacrylonitrile; polyphenyleneoxides such as those prepared from 2,6-dimethylphenol and the like; and copolymers such as those of polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., di(1,2-ethylene)-azelate, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., $\beta$-methoxyethyleneglycol, methoxytriethyleneglycol, triethylene glycol, octaethyleneglycol, dibutyleneglycol, dipropyleneglycol and the like.

The compounds of this invention are particularly useful as UV light stabilizers, especially for the protection of polyolefins, for instance, polyethylene, polypropylene, poly(butene-1), poly(pentene-1), poly (3-methylbutene-1), poly(4-methylpentene-1), various ethylene-propylene copolymers and the like.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, blow molded or the like into films, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, sulfur-containing esters such as distearyl-$\beta$-thiodipropionate (DSTDP), dilauryl-$\beta$-thiodipropionate (DLTDP) in an amount of from 0.01 to 2% by weight of the organic material, and the like, pourpoint depressants, corrosion and rust inhibiotors, dispersing agents, demulsifiers, antifoaming agents, fillers such as glass or other fibers, carbon black, accelerators and the other chemicals used in rubber compounding, plasticizers, color stabilizers, di- and tri-alkyl- and alkylphenylphosphites, heat stabilizers, ultraviolet light stabilizers, antiozonants, dyes, pigments, metal chelating agents, dyesites and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

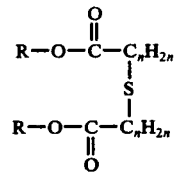

wherein R is an alkyl group having from 6 to 24 carbon atoms; and n is an integer from 1 to 6. Especially useful compounds of this type are dilauryl-$\beta$-thiodipropionate and distearyl-$\beta$-thiodipropionate. The above co-stabilizers are used in the amount of from 0.01 to 2% by weight of the organic material, and preferably from 0.1 to 1%.

Although the compounds of this invention may to some degree also be effective as thermal stabilizers, if the processing of the polymer is carried out at high temperatures it is advantageous to incorporate additional antioxidants.

In most applications, it is desirable to incorporate into the resin composition, sufficient thermal antioxidants to protect the plastic against thermal and oxidative degradation. The amount of antioxidant required will be comparable to that of the actinic stabilizer. Namely, from about 0.005% to 5% and preferably from 0.01% to 2% by weight. Representative of such antioxidants are phosphite esters, such as triphenylphosphite and dibutylphosphite and alkyl arylphosphites such as dibutylphenylphosphite, and the like.

The best results have been obtained with the preferred class of thermal antioxidants, the hindered phenols. These compounds have been found to provide the best thermal stabilization with the least discoloration in the compositions of the invention. Amoung these phenolic antioxidants are included the following:

di-n-octadecyl(3-5-butyl-4-hydroxy-5-methylbenzyl)-malonate
2,6-di-t-butylphenol
2,2'-methylene-bis(6-t-butyl-4-methylphenol)
2,6-di-t-butylhydroquinone
octadecyl-(3,5-di-t-butyl-4-hydroxybenzylthio)acetate
1,1,3-tris(3-t-butyl-6-methyl-4-hydroxyphenyl)butane
1,4-bis(3,5-di-t-butyl-4-hydroxybenzyl)-2,3-5,6-tetramethylbenzene
2,4-bis-(3,5-di-t-butyl-4-hydroxyphenoxy)-6-(n-octylthio)-1,3,5-triazine
2,4-bis-(4-hydroxy-3,5-di-t-butylphenoxy)-6-(n-octylthioethylthio)-1,3,5-triazine
2,4-bis-(n-octylthio)-6-(3,5-di-t-butyl-4-hydroxyanilino)-1,3,5-triazine
2,4,6-tris-(4-hydroxy-3,5-di-t-butylphenoxy)-1,3,5-triazine
n-octadecyl-β-(3,5-di-t-butyl-4-hydroxyphenyl) propionate
n-octadecyl-3,5-di-t-butyl-4-hydroxybenzoate
2-(n-octylthio)ethyl-3,5-di-t-butyl-4-hydroxybenzoate
stearamido N,N-bis-{ethylene 3-(3,5-di-t-butyl-4-hydroxyphenyl)propionate}
1,2-propylene glycol bis-{3-(3,5-di-t-butyl-4-hydroxyphenyl)propionate}
pentaerythritol tetrakis-{3-(3,5-di-t-butyl-4-hydroxyphenyl)propionate}
dioctadecyl-3,5-di-t-butyl-4-hydroxybenzylphosphonate
di-n-octadecyl-1-(3,5-di-t-butyl-4-hydroxyphenyl)-ethanephosphonate The above phenolic hydrocarbon stabilizers are known and many are commercially available.

The above antioxidants have been listed only for the purpose of illustration and it is important to note that any other antioxidant can be employed with similar improved results. The above exemplified antioxidants and other related antioxidants which are incorporated herein by reference, are disclosed in greater detail in the following patents: Netherlands Pat. No. 67/1119, issued Feb. 19, 1968; Netherlands Pat. No. 68/03498 issued Sept. 18, 1968; U.S. Pat. Nos. 3,255,191; 3,330,859, 3,644,482, 3,281,505; 3,531,483; 3,285,855; 3,364,250; 3,368,997; 3,357,944 and 3,758,549.

The compounds of this invention may be prepared by reacting a piperidinol of the formula.

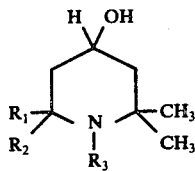

II wherein $R_1$, $R_2$, and $R_3$ are as defined above via a usual esterification procedure with a diacid of the formula

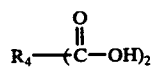

III wherein $R_4$ is as defined above, or conveniently with a acid anhydride in the case of diglycolic anhydride and the like. In the process of reacting an acid of formula III with a compound of formula II the esterification catalyst is preferably a neutral catalyst, for instance a tetraalkyl titanate.

The acids and acid anhydrides which are reacted with the compounds of formula II may be prepared by methods well known in the art.

The metal salts of the present invention can be prepared by treating the hindered piperidine carboxylic acids of formula I with a reactive form of the metal or metal complex, e.g., sodium hydroxide or the like. Alternatively, and preferably in the case of metal complexes and metals other than the alkali metals, a double decomposition is employed. Thus, for example, a sodium salt of the present invention is treated with nickel chloride. In a similar fashion use of other halides such as manganese dichloride, barium chloride and the like results in formation of the corresponding metal derivative.

The compounds of formula II may be prepared according to procedures presented in patent application Ser. No. 408,123, filed Oct. 19, 1973.

The following examples, presented for illustration and not limitation, will further serve to typify the nature of the present invention.

EXAMPLE 1

O-mono-(2,2,6,6-tetramethyl-piperidin-4-ol)sebacate

A. In a 3 liter 3-necked flask equipped with a stirrer, thermometer, condenser with water separator and drying tube, and nitrogen inlet tube were placed a mixture of 161.6 g (0.8 moles) of sebacic acid, 50.4 g (0.32 moles) of 2,2,6,6-tetramethylpiperidin-4-ol and 2000 ml of xylene. To the mixture was added 9.6 ml (0.032 moles) of tetraisopropyl titanate. The reaction mixture was heated under reflux with stirring and 6.0 ml of water were collected over a 30 hour period. The reaction mixture was cooled and the xylene was removed by decantation. The residue was recrystallized from warm dimethylformamide, then from isopropanol, yielding 26.9 g of white crystals, m.p. 174° to 178° C of the desired material.

B. By following the above procedure (A), and substituting for the sebacic acid an equivalent amount of:
   a. pimelic acid
   b. tetramethyl succinic acid
   c. azelaic acid
   d. thiodipropionic acid
   e. suberic acid
   f. thiodiglycolic acid
there is respectively obtained the following compounds:

a. o-mono(2,2,6,6-tetramethyl-piperidin-4-ol)pimelate
b. o-mono(2,2,6,6-tetramethyl-piperidin-4-ol)tetramethyl succinate
c. o-mono(2,2,6,6-tetramethyl-piperidin-4-ol)azelate
d. o-mono(2,2,6,6-tetramethyl-piperidin-4-ol)thiodipropionate
e. o-mono(2,2,6,6-tetramethyl-piperidin-4-ol)suberate
f. o-mono(2,2,6,6-tetramethyl-piperidin-4-ol)thiodiglycoate.

C. By essentially following the above procedure (A), and substituting the reactants appropriate quantities of the following reagents a. 1-n-dodecyl-2,2,6,6-tetramethyl piperidin-4-ol and sebacic acid b. 1-benzyl-2,2,6,6-tetramethyl piperidin-4-ol and azelaic acid
c. 1-allyl-2,2,6,6-tetramethyl piperidin-4-ol and suberic acid there are respectively obtained and following compounds:
a. o-mono(1-n-dodecyl-2,2,6,6-tetramethylpiperidin-4-ol)sebacate.
b. o-mono(1-benzyl-2,2,6,6-tetramethyl piperidin-4-ol) azelate.
c. o-mono(1-allyl-2,2,6,6-tetramethyl piperidin-4-ol) suberate.

EXAMPLE 2

O-mono(1,2,2,6,6-pentamethyl-piperidyl-4)diglycolate

In a 1 liter 3-necked flask equipped with a stirrer, thermometer, condenser with water separator and drying tube, and nitrogen inlet, was placed 18.93 g (0.10 moles) of 1,2,2,6,6-pentamethyl-piperidine-4-ol monohydrate and 500 ml of xylene. The reaction mixture was heated under reflux with stirring until 1.8 ml of water had been collected in the water separator. The reaction mixture was cooled to 40° C and 11.6 g (0.10 moles) of diglycolic anhydride were added. The reaction mixture was heated slowly to reflux. The anhydride appeared to go into solution; then a precipitate was noted. The reaction mixture was heated under reflux for 4 hours and allowed to cool overnight. The precipitated solids were collected by suction, washed with hexane and dried in air. The product was recrystallized from ethanol-isopropanol, and dried under vacuum at 60° C over $P_2O_5$, yielding 14.7 g of colorless crystals, m.p. 194°–198° C, of the desired material.

EXAMPLE 3

Nickel bis(o-mono-(2,2,6,6-tetramethyl-piperidin-4-ol)sebacate)

A. In a 2 liter 3-necked flask equipped with a thermometer, dropping funnel, stirrer and nitrogen inlet were placed 20.49 g (0.06 moles) of o-mono(2,2,6,6-tetramethylpiperidin-4-ol)sebacate and 1200 ml of absolute methanol. To the mixture was added via pipette 60 ml of 1 N KOH in methanol. To the clear solution was then added a solution of 7.13 g (0.03 moles) of $NiCl_2 6H_2O$ in 120 ml of absolute methanol over a 10 minute period. The reaction mixture was stirred at room temperature for 1 hour and at 50° C for 1 hour. The green methanolic solution was then evaporated under reduced pressure and 1200 ml of isopropanol was added. The isopropanol solution was heated to 50° C for 1 hour and allowed to stand overnight. The isopropanol solution was filtered with suction and the filtrate evaporated under reduced pressure. The residue was treated with 850 ml of benzene, filtered with suction, and the benzene solution evaporated under reduced pressure and dried at 70° C under vacuum, yielding 18.5 g of a pale green glassy solid of the desired material.

B. By following the above procedure (A) and substituting for the o-mono-(2,2,6,6-tetramethylpiperidin-4-ol)sebacate an equivalent amount of:

a. o-mono-(2,2,6,6-tetramethyl-piperidin-4-ol)pimelate
b. o-mono(2,2,6,6-tetramethyl-piperidin-4-ol)tetramethyl succinate
c. o-mono(2,2,6,6-tetramethyl-piperidin-4-ol)thiodiglycolate
d. o-mono(1-n-dodecyl-2,2,6,6-tetramethyl-piperidin-4-ol)sebacate
e. o-mono(1-benzyl-2,2,6,6-tetramethyl piperidin-4-ol)azelate
f. o-mono(1-allyl-2,2,6,6-tetramethyl piperidin-4-ol)suberate.

There is respectively obtained the following compounds:

a. nickel complex of o-mono(2,2,6,6-tetramethyl-piperidin-4-ol)pimelate
b. nickel complex of o-mono(2,2,6,6-tetramethyl-piperidin-4-ol)tetramethyl succinate
c. nickel complex of o-mono(2,2,6,6-tetramethyl-piperidin-4-ol)thiodiglycolate.
d. nickel complex of o-mono(1-n-dodecyl-2,2,6,6-tetramethyl piperidin-4-ol)sebacate
e. nickel complex of o-mono(1-benzyl-2,2,6,6-tetramethyl piperidin-4-ol)azelate
f. nickel complex of o-mono(1-allyl-2,2,6,6-tetramethyl piperidin-4-ol)suberate.

EXAMPLE 4

By essentially following the procedure of Example 3 (A) and substituting the following metal complexes for nickel chloride:
a. manganese chloride
b. zinc chloride
c. ferric chloride
d. cobalt (ous) chloride
there is thus respectively obtained:

a. manganese complex of bis{o-mono (2,2,6,6-tetramethylpiperidin-4-ol)sebacate}
b. zinc complex of bis{o-mono(2,2,6,6-tetramethyl-piperidin-4-ol)sebacate}
c. iron complex of bis{o-mono(2,2,6,6-tetramethyl-piperidin-4-ol)sebacate}
d. cobalt comples of bis{o-mono(2,2,6,6-tetramethyl-piperidin-4-ol)sebacate}.

EXAMPLE 5

Ni (II) bis{o-mono-(1,2,2,6,6-Pentamethylpiperidin-4-ol)diglycolate}

In a 100 ml 1-necked flask equipped with a magnetic stirrer and distillation head were placed 2.87 g (0.01 moles) of o-mono-(1,2,2,6,6-tetramethylpiperidin-4-ol)diglycolate, 1.26 g (0.005 moles) of nickel acetate tetrahydrate and 50 ml of water. The reaction mixture was heated slowly to distillation temperature. The distillate collected was assayed by titration with 0.1 N KOH with phenophthalein as indicator. The distillation was continued until 98% of the theoretical amount of acetic acid had been collected. The reaction mixture was then evaporated under vacuum, and the residue dissolved in methanol, filtered and the filtrate evaporated under reduced pressure. The green powdery residue, m.p. 210° (d) weighed 3.28 g and proved to be the desired material.

EXAMPLE 6

ARTIFICIAL LIGHT EXPOSURE TEST

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The tests conducted on polymers using an artificial light exposure device is described below:

a. Sample Preparation 5 mil Film - Unstabilized polypropylene powder (Hercules Profax 6501) is thoroughly blended with the indicated amounts of additives. The blended material is then milled on a 2 roll mill for 5 minutes at 182° C. The milled sheet is then compression molded at 220° C into 5 mil thick film under a pressure of 175 psi and water cooled in the press.

b. Testing Method

This test is conducted in a FS/BL unit, basically of the American Cyanamid design, which consists of 40 tubes of alternating fluorescent sunlamps and black lights (20 of each). The 5 mil sample film which are mounted on 3 × 2 inch IR card holders with $\frac{1}{4}$ × 1 inch windows and are placed on a rotating drum 2 inches from the bulbs in the FS/BL unit. The time in hours is noted for the development of 0.5 carbonyl absorbance units as determined on an Infrared Spectophotometer. The development of carbonyl functional groups in the polymer is proportional to the amount of degradation caused by the ultraviolet light exposure.

The test results reported below were obtained according to the procedures described above. The amounts of the additives are expressed in weight percent based on the weight of the polymer.

TABLE I

Light Stabilization Data in Polypropylene

| Additive | Time in Hours to 0.5 Carbonyl Absorbance Units | |
|---|---|---|
| | Formulation A* | Formulation B** |
| o-mono(2,2,6,6-tetra-methylpiperidin-4-ol)sebacate | 2330 | 2495 |
| nickel bis{o-mono(2,2,6,6-tetramethylpiperidin-4-ol)sebacate} | 3635 | 2335 |
| o-mono(1,2,2,6,6-pentamethyl piperidin-4-ol)diglycolate | 1295 | 1420 |
| nickel bis{o-mono(1,2,2,6,6-pentamethyl piperidin-4-ol)diglycolate} | 565 | 1125 |
| Blank | 215 | — |

*Formulation A contains 0.5% additive and 0.2% antioxidant dioctadecyl 3,5-di-t-butyl-4-hydroxybenzylphosphonate.
**Formulation B contains 0.25% additive, 0.25% UV absorber 2(2'-hydroxy-3',5'-di-t-butyl-phenyl)-5-chlorobenzotriazole, and 0.2% antioxidant dioctadecyl 3,5-di-t-butyl-4-hydroxybenzyl-phosphonate.
Proportionately good stabilization is obtained when in the Compositions of Table I the compounds of this invention are present in the concentrations of 0.1% and 1%.

Other hindered phenolic antioxidants may be used in place of di-octadecyl(3,5-di-t-butyl-4-hydroxybenzyl)-phosphonate in the above mentioned compositions for example, di-n-octadecyl α-(3-t-butyl-4-hydroxy-4-methylbenzyl)malonate, 2,4-bis(n-octylthio)-6-(3,4-di-t-butyl-4-hydroxyaniline)-1,3,5-triazine, octadecyl 3-(3',5'-di-t-butyl-4'-hydroxyphenyl)propionate, pentaerythritol-tetrakis{3-(3,5-di-t-butyl-4-hydroxyphenyl)}propionate, tris-(3,5-di-t-butyl-4-hydroxybenzyl)isocyanurate, 2,6-di-tert-butyl-4-methylphenol, N,N,N-tris-(3,5-di-tert-butyl-4-hyroxybenzyl)isocyanurate, and 2,4,6-tris(3,5-di-tert-butyl-4-hyroxybenzyl)-1,3,5-trimethylbenzyl.

The compositions of Table I are also stabilized with 2(2'-hydroxy-3',5'-di-t-butylphenyl)-5-chlorobenzotriazole is replaced with the following UV absorbers:

a. 2-hydroxy-4-methoxy-5-sulfobenzophenone trihydrate
b. 2-hydroxy-4-n-octoxybenzophenone
c. {2,2'-thiobis(4-t-octylphenolate)}-n-butylamine nickel II
d. p-octylphenyl salicylate
e. 2,2'-dihydroxy-4,4'-dimethoxybenzophenone
f. 2(2'-hydroxy-5'-methylphenyl)-benzotriazole.

EXAMPLE 7

High impact polystyrene resin containing elastomer (i.e., butadiene-styrene) is stabilized against loss of elongation properties due to exposure to ultraviolet light by incorporation of 0.3% by weight of o-mono-(2,2,6,6-tetramethylpiperidin-4-ol)sebacate.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C and a pressure of 2,000 pounds per square inch into a sheet of uniform thickness (25 mil). The sheets are then cut into strips approximately 4 × 0.5 inches. A portion of these strips is then measured for percent of elongation in the Instron Tensile Testing Apparatus (Instron Engineering Corporation, Qunicy, Mass.). The remaining portions of the strips are placed in an FS/BL chamber according to Example 6(B) except that the samples are mounted and white cardboard stock and the time to 50% reduction in elongation is measured. The stabilized polystyrene resin retains its elongation property longer than the unstabilized resin.

EXAMPLE 8

Unstabilized linear polyethylene is solvent blended in methylene chloride with 0.5% by weight of the substrate of the nickel complex of o-mono(2,2-6,6-tetramethylpiperidin-4-ol)sebacte and then vacuum dried. The resin is then extrusion compounded on a 1 inch 24/1=L/D extruder, melt temperature 450° F (232° C) and pressed for 7 minutes at a temperature of 163° C and a pressure of 2000 psi into a sheet of uniform thickness of 100 mil. The sheets are then cut into plaques of 2 inch × 2 inch. The plaques are then exposed in a FS/BL exposure device and color measurements made periodically using a Hunter Color Difference Meter Model D25. Polyethylene stabilized with the above compound is found to be much more stable than the unstabilized polyethylene or the polyethylene stabilized only with an antioxidant. EXAMPLE 9

A quantity of SBR emulsion containing 100 g of rubber (500 ml of 20% SBR obtained from Texas U.S., Synpol 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (>1 mm) at 40°–45° C.

The dried rubber (25 g) is heated under nitrogen at 125° C in a Brabender mixer and to this is added with mixing 0.25 g (0.5%) of o-mono(1,2,2,6,6-pentamethyl piperidin-4-ol)diglycolate. is mixed for 5 minutes after which it is cooled and compression molded at 125° C into 5 × 0.025 inch plaques.

The plaques are exposed to a xenon arc weatherometer and the color measurements (L-b) is made after 45, 125 and 290 hours. The samples stabilized with the above compound are found to be much more light stable than the unstabilized samples.

EXAMPLE 10

To 50 g of polyacetal resin containing 0.1% of an acid scavenger, dicyandiamide, is added 0.2% by weight of the nickel complex of o-mono(2,2,6,6-tetramethyl-piperidin-4-ol)thiodiglycolate and milled for 7 minutes at 200° C in a Brabender Plasti-recorder. The milled formulation is subsequently pressed into a 40 mil sheet at 215° C at 350 psi for 90 seconds then cooled quickly in a cold press at 350 psi. The stabilized sheets are then remolded for 2 minutes at contact pressure and for 3 minutes at 300 psi at 215° C to give plaques 1½ inch × 2¼ inch × 125 mil. Thereafter, the testing procedure of Example 8 is followed to determine the light stability of the samples. The stabilized samples are found to be much more stable than the unstabilized samples.

EXAMPLE 11

Unstabilized thoroughly dried polyethylene terephthalate chips are dry blended with 1.0% of o-mono(2,2,6,6-tetramethylpiperidin-4-ol)suberate. 60/10 denier multifilament is melt spun at a melt temperature of 290° C. The oriented fiber is wound on white cards and exposed in a Xenon Arc Fadeometer. Color measurements are made periodically with a Hunter Color Difference Meter Model D25. The stabilized samples are found to be much more light stable than the unstabilized samples.

EXAMPLE 12 a. A composition comprising acrylonitrile-butadiene-styrene terpolymer and 1% by weight of the nickel complex of o-mono(1,2,2,6,6-pentamethyl piperidin-4-ol)diglycolate resists embrittlement due to exposure to ultraviolet light longer than one which does not contain the stabilizer. b. A composition comprising polyurethane prepared from toluene diisocyanate and alkylene polyols and 1.0% by weight of o-mono(2,2,6,6-tetramethyl-piperidin-4-ol)tetramethyl succinate is more stable to sunlight, fluorescent sunlamps, black lights and fluorescent lights than the unformulated polyurethane. c. A composition comprising a polycarbonate prepared from bisphenol-A and phosgene and 1% by weight of o-mono(2,2,6,6-tetramethyl-piperidin-4-ol)pimelate resists discoloration due to exposure to ultraviolet light longer than one which does not contain the stabilizer. d. A composition comprising polymethyl-methacrylate and 0.25% by weight of the nickel complex of o-mono(2,2,6,6-tetramethyl-piperidin-4-ol)azelate resists discoloration due to exposure to ultraviolet light longer than one which does not contain the stabilizer.

EXAMPLE 13 a. A stabilized polyamide (nylon 6,6) is prepared by incorporating therein 0.1% of o-mono(2,2,6,6-tetramethyl-piperidin-4-ol)sebacate. The light stability of the stabilized composition is superior to that of an unstabilized polyamide. b. A stabilized polyphenylene oxide polymer (prepared by polymerizing 2,6-dimethylphenol is prepared by incorporating therein 0.5% by weight of the manganese complex of o-mono(2,2,6,6-tetramethyl-piperidin-4-ol)sebacate. The stabilized compositions resist embrittlement due to exposure to ultraviolet light longer than one which does not contain the stabilizer. c. A stabilized crystalline polystyrene is prepared by incorporating therein 0.1% by weight of the zinc complex of o-mono(2,2,6,6-tetramethyl-piperidin-4-ol)sebacate. The stabilized composition resists embrittlement due to exposure to ultraviolet light longer than one which does not contain the stabilizer.

Antioxidants may also be incorporated into each of the above mentioned compositions, for example, di-n-octadecyl-α,α'-bis(3-butyl-4-hydroxy-5-methylbenzyl) malonate 2,4-bis(4-hydroxy-3,5-di-t-butylphenoxy)-6-(n-octylthioethylthio)-1,3,5-triazine, 2,4-bis(3,5-di-t-butyl-hydroxyphenoxy)-6-(n-octylthio)-1,3,5-triazine di-n-octadecyl 3(3',5'-di-t-butyl-4-hydroxyphenyl)propionate, respectively.

What is claimed is:

1. A composition of matter comprising a synthetic organic polymer normally subject to ultraviolet deterioration stabilized with 0.005 to 5% of a stabilizer having the formula

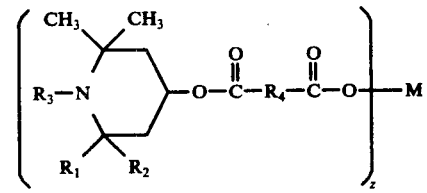

wherein
  $R_1$ and $R_2$ independently of each other are straight- or branched-chain alkyl having from 1 to 6 carbon atoms, or together with the carbon to which they are bound form a cyclopentyl or cyclohexyl ring, which is unsubstituted or substituted with a methyl group,
  $R_3$ is hydrogen, alkyl having 1 to 12 carbon atoms, β-methoxyethyl, alkenyl having 3 to 4 carbon atoms, propargyl, benzyl, or alkyl substituted benzyl,
  $R_4$ is straight- or branched-chain alkylene having 5 to 8 carbon atoms, or the group $(CH_2)_mY(CH_2)_n$ wherein Y is oxygen or sulfur and $m$ and $n$ independently of each other are an integer of from 1 to 3,
  M is hydrogen or a metal selected from the group consisting of barium, nickel, manganese, calcium, zinc, iron, sodium, cobalt, tin and dialkyl tin, and
  $z$ has a value of from 1 to 4, the value of $z$ being the same as the available valence of M said stabilizer bing incorporated into the synthetic organic polymer after polymerization.

2. The composition of claim 1 which contains additionally 0.005 to 5% of a phenolic antioxidant.

3. The composition of claim 1 which contains additionally a. 0.005 to 5% of a phenolic antioxidant, and
b. a stabilizing amount of a UV absorber selected from the group consisting of hydroxy benzophenones, hydroxyphenyl benzotriazoles, aromatic esters of salicyclic acid and nickel amine complexes of thiobis-phenols.

4. The composition of claim 1 which contains additionally
a. 0.005 to 5% of a phenolic antioxidant, and
b. 0.01 to 2% of a thio co-stabilizer of the formula

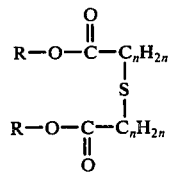

wherein R is an alkyl group having from 6 to 24 carbon atoms and $n$ is an integer from 1 to 6.

5. The composition of claim 1 wherein the synthetic organic polymer is a polyolefin.

6. The composition of claim 5 wherein the polyolefin is polypropylene.

7. The composition of claim 5 which contains additionally 0.005 to 5% of a phenolic antioxidant selected from the group consisting of n-octadecyl 3-(3,5-di-t-butyl-4-hydroxyphneyl propionate, di-n-octadecyl(3,5-di-t-butyl-4-hydroxybenzyl) phosphonate, pentaerythritol-tetrakis[3,5-di-t-butyl-4-hydroxyphenyl)propionate] and tris-(3,5-di-t-butyl-4-hydroxybenzyl)isocyanurate.

8. The composition of claim 5 which contains additionally
a. 0.005 to 5% of a phenolic antioxidant selected from the group consisting of n-octadecyl 3-(3,5-di-t-butyl-4-hydroxyphenyl)propionate, di-n-octadecyl(3,5-di-t-butyl-4-hydroxybenzyl)phosphonate, pentaerythritol-tetrakis[(3-3,5-di-t-butyl-4-hydroxyphenyl)propionate] and tris-(3,5-di-t-butyl-4-hydroxybenzyl)isocyanurate, and
b. a stabilizing amount of a UV absorber selected from the group consisting of 2(2'-hydroxy-3',5'-di-tert-butylphenyl)-5-chlorobenzatriazole, 2(2'-hydroxy-5'-methylphenyl)-benzotriazole, and 2-hydroxy-4-n-octoxybenzophenone.

9. The composition of claim 5 wherein $R_1$ and $R_2$ are each methyl.

10. The composition of claim 9 wherein $R_4$ is straight-chain alkylene having 5 to 8 carbon atoms, or the group $(Ch_2)_mY(Ch_2)_n$ where Y is oxygen or sulfur and $m$ and $n$ independently of each other are 1 to 2, M is hydrogen, nickel or manganese, and Z has a value of 1 or 2.

11. The composition of claim 10 wherein M is nickel.

12. The composition of claim 10 wherein M is hydrogen.

13. The composition of claim 10 wherein $R_4$ is straight-chain alkylene having 5 to 8 carbon atoms.

14. The composition of claim 10 wherein $R_4$ is the group $(Ch_2)_mY(CH_2)_n$ is Y, $m$ and $n$ are defined in claim 24.

15. The composition of claim 5 wherein the stabilizer is o-mono(2,2,6,6-tetramethyl-piperidin-4-ol)sebacate.

16. The composition of claim 5 wherein the stabilizer is nickel bis[o-mono(2,2,6,6-tetramethylpiperidin-4-ol) sebacate].

17. The composition of claim 5 wherein the stabilizer is o-mono(1,2,2,6,6-pentamethyl piperidin-4-ol)diglycolate.

18. The composition of claim 5 wherein the stabilizer is nickel bis[o-mono(1,2,2,6,6-pentamethylpiperidin-4-ol) diglycolate].

19. A compound of the formula

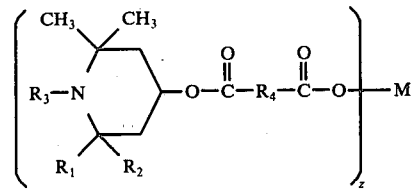

wherein
$R_1$ and $R_2$ independently of each other are straight- or branched-chain alkyl having from 1 to 6 carbon atoms, or together with the carbon to which they are bound form a cyclopentyl or cyclohexyl ring, which is unsubstituted or substituted with a methyl group.
$R_3$ is hydrogen, alkyl having 1 to 12 carbon atoms, β-methoxyethyl, alkenyl having 3 or 4 carbon atoms, propargyl, benzyl, or alkyl substituted benzyl,
$R_4$ is straight- or branched-chain alkylene having 5 to 8 carbon atoms, or the group $(CH_2)_mY(CH_2)_n$ wherein Y is oxygen or sulfur and $m$ and $n$ independently of each other are an integer of from 1 to 2,
M is hydrogen or a metal selected from the group consisting of barium, calcium, and sodium, and the value of $z$ is the same as the available valence of M.

20. A compound according to claim 19 wherein $R_1$ and $R_2$ are each methyl.

21. A compound according to claim 20 wherein $R_4$ is straight-chain alkylene having 5 to 8 carbon atoms, or the group $(CH_2)_mY(CH_2)_n$ wherein Y is oxygen or sulfur and $m$ and $n$ independently of each other are 1 and 2, and $z$ has a value of 1 or 2.

22. A compound according to claim 21 wherein M is hydrogen.

23. A compound according to claim 20 wherein $R_4$ is straight-chain alkylene having 5 to 8 carbon atoms.

24. A compound according to claim 21 wherein $R_4$ wherein $R_4$ is the group $(CH_2)_mY(CH_2)_n$ and Y, $m$ and $n$ are as defined in claim 35.

25. A compound according to claim 21 which is o-mono-(2,2,6,6-tetramethyl-piperidin-4-ol)sebacate.

26. A compound according to claim 21 which is o-mono (1,2,2,6,6-pentamethyl piperidin-4-ol)diglycolate.

* * * * *